US012605322B2

(12) United States Patent
Springob et al.

(10) Patent No.: US 12,605,322 B2
(45) Date of Patent: Apr. 21, 2026

(54) SHAMPOO COMPOSITION WITH NON-SULFATE SURFACTANT AND COMPLEXATION COMPOUND FORMING A COACERVATE

(71) Applicant: Wella International Operations Switzerland Sarl, Petit-Lancy (CH)

(72) Inventors: Christian Springob, Lorsch (DE); Marion Stuess, Griesheim (DE); Malte Dirk Benjamin Koch, Taunusstein (DE); Antonio Martinez-Campoy, Rüsselsheim (DE); Esther Mattke, Groß-Gerau (DE)

( * ) Notice: Subject to any disclaimer, the term of this patent is extended or adjusted under 35 U.S.C. 154(b) by 893 days.

(21) Appl. No.: 17/267,685

(22) PCT Filed: Aug. 8, 2019

(86) PCT No.: PCT/EP2019/071298
§ 371 (c)(1),
(2) Date: Feb. 10, 2021

(87) PCT Pub. No.: WO2020/030732
PCT Pub. Date: Feb. 13, 2020

(65) Prior Publication Data
US 2021/0315791 A1 Oct. 14, 2021

Related U.S. Application Data

(60) Provisional application No. 62/717,515, filed on Aug. 10, 2018.

(51) Int. Cl.
| | |
|---|---|
| *A61K 8/46* | (2006.01) |
| *A61G 5/02* | (2006.01) |
| *A61K 8/41* | (2006.01) |
| *A61K 8/42* | (2006.01) |
| *A61K 8/73* | (2006.01) |
| *A61Q 5/00* | (2006.01) |
| *A61Q 5/02* | (2006.01) |
| *A61Q 5/12* | (2006.01) |

(52) U.S. Cl.
CPC ............... *A61K 8/466* (2013.01); *A61G 5/02* (2013.01); *A61K 8/416* (2013.01); *A61K 8/42* (2013.01); *A61K 8/737* (2013.01); *A61Q 5/006* (2013.01); *A61Q 5/12* (2013.01); *A61K*
*2800/30* (2013.01); *A61K 2800/5424* (2013.01); *A61K 2800/5426* (2013.01)

(58) Field of Classification Search
CPC .......... A61K 8/466; A61K 8/416; A61K 8/42; A61K 8/737; A61K 2800/5424; A61K 2800/5426; A61Q 5/006; A61Q 5/02; A61Q 5/12
See application file for complete search history.

(56) References Cited

U.S. PATENT DOCUMENTS

| | | | | |
|---|---|---|---|---|
| 4,259,204 A | * | 3/1981 | Homma ................. | A61K 8/463 |
| | | | | 510/122 |
| 6,284,230 B1 | | 9/2001 | Sako et al. | |
| 6,455,058 B1 | * | 9/2002 | Sun ........................ | A61Q 5/006 |
| | | | | 424/70.21 |
| 2007/0160555 A1 | * | 7/2007 | Staudigel ............... | A61K 8/732 |
| | | | | 424/70.13 |
| 2015/0157548 A1 | | 6/2015 | De Feij et al. | |
| 2016/0229929 A1 | * | 8/2016 | Schubert .............. | C11D 3/0015 |

FOREIGN PATENT DOCUMENTS

| | | | | |
|---|---|---|---|---|
| EP | 0256656 A1 | 2/1988 | | |
| GB | 2055119 A | * | 2/1981 | ............... C11D 1/62 |
| JP | 03281700 A | * | 12/1991 | ............... C11D 1/94 |
| WO | 9726854 | 7/1997 | | |

OTHER PUBLICATIONS

JP 03281700 A machine translation (Year: 1991).*
International Search Report issued in connection with PCT Application PCT/EP2019/071298 dated Oct. 7, 2019.
Bumble and Bumble: "Sulfate Free Shampoo," GNPD, Mintel, Feb. 1, 2016, XP002783430, Abstract.
"LT High Performance Hair Stimulating Shampoo," GNPD, Mintel, Jan. 31, 2014, XP002770577, Abstract.

* cited by examiner

*Primary Examiner* — Mina Haghighatian
*Assistant Examiner* — Nathan W Schlientz
(74) *Attorney, Agent, or Firm* — Dennemeyer & Associates LLC

(57) ABSTRACT

A non-sulfate shampoo is disclosed. The shampoo incorporates at least one non-sulfate surfactant selected from a taurate salt and a sarcosinate salt, and in addition incorporates a complexation compound. The shampoo produces a coacervate upon dilution with water and in use to shampoo hair. The shampoo provides mild non-irritating treatment of the hair and does not irritate skin or eyes.

14 Claims, No Drawings

SHAMPOO COMPOSITION WITH NON-SULFATE SURFACTANT AND COMPLEXATION COMPOUND FORMING A COACERVATE

CROSS-REFERENCE TO RELATED APPLICATIONS

This is a 35 U.S.C. 371 National Stage Patent Application of International Application No. PCT/EP2019/071298, filed Aug. 8, 2019, which claims priority to U.S. Provisional application 62/717,515, filed Aug. 10, 2018, each of which is hereby incorporated by reference in its entirety.

FIELD OF THE INVENTION

A sulfate free shampoo composition composed of amino acid amides and a complexation compound such as a cationic compound which is capable for forming improved hair conditioning while avoiding harsh treatment of hair and skin that often is associated with detersive sulfate surfactant shampoos.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy", and a loss of luster, due to removal of natural oils or other hair moisturizing materials.

After shampooing, the hair can also suffer from a loss of "softness" perceived by the user upon drying. The hair can also suffer from increased levels of static upon drying after shampooing. This can interfere with combing and can result in "fly-away" hair. A variety of approaches have been developed to alleviate the after-shampoo problems. These range from the inclusion of hair conditioning aids in shampoos to post-shampoo application of hair conditioners, i.e., hair rinses.

Conditioning shampoos or "2 in 1" hair products comprising detersive sulfate surfactants and hair conditioning agents are known as possible answers to the problem of dry, frizzy hair. These personal care compositions typically comprise an anionic detersive sulfate surfactant in combination with a conditioning agent such as a silicone, hydrocarbon oil, fatty esters etc. These products have become more popular among consumers as a means of conveniently obtaining hair conditioning and cleansing performance from a single product.

Many of these conditioning shampoo compositions, however, are harsh on the skin, remove essential oils and emollients from the hair and skin and have an undue drying effect. Such shampoos also do not provide sufficient deposition of conditioning agents onto hair or skin during the application process. Generally, these conditioning shampoos do not enable hair conditioning without significant amounts of conditioner and can leave the hair dry, frizzy and without the softness and acceptable feel expected for gently treated clean hair.

While a wide variety of shampoos have been disclosed which contain conditioning aids, they have not been totally satisfactory for a variety of reasons. Cationic conditioning agents are highly desirable for use in hair conditioning due to their abilities to control static, improve wet detangling, and provide a silky wet hair feel to the user. One problem which has been encountered in shampoos relates to compatibility problems between good cleaning anionic surfactants and the many conventional cationic agents which historically have been used as conditioning agents. Efforts have been made to minimize adverse interaction through the use of alternate surfactants and improved cationic conditioning agents. Cationic surfactants which provide good overall conditioning in hair rinse products, in general, tend to complex with anionic cleaning surfactants and provide poor conditioning in a shampoo context. In particular, the use of soluble cationic surfactants that form soluble ionic complexes do not deposit well on the hair Soluble cationic surfactants that form insoluble ionic complexes deposit on the hair but do not provide good hair conditioning benefits and tend to cause the hair to have a dirty, coated feel.

Consequently, needs exist for a conditioning shampoo composition that provides excellent hair softening, conditioning and optional anti-dandruff performance without harsh, drying activity that can remove essential oils and emollients from the hair and skin and leave an untoward foci to the hair.

SUMMARY OF THE INVENTION

According to a first aspect, the present invention relates to a method of achieving improved hair feel and cleanliness by application to the hair of embodiments of the shampoo composition of the invention. Component embodiments of the shampoo composition include (a) a non-sulfate surfactant and (b) a complexation compound. The compositional embodiments can but not necessarily include optional components such as a co-surfactant and/or antidandruff agent. The co-surfactant may be a nonionic co-surfactant, a betaine, a sultaine, a fatty acid polyol or an amphoteric co-surfactant. The component embodiments of the composition of the invention are formulated in an aqueous medium at concentrations ranging from low to moderate. The embodiments of the composition of the invention do not include a detersive anionic sulfate surfactant such as but not limited to sodium lauryl sulfate, nor do they include any kind of silicone conditioner including but not limited to aminosilicones, silicone block copolymers with hydrophilic organic blocks and silicones containing only pendant alkyl groups.

The non-sulfate anionic surfactant is an amino carboxylic acid derivative or an amino sulfonic acid derivative such as an N-fatty acyl taurate salt or a N-fatty acyl sarcosinate salt, the N-alkyl derivative of either salt or a combination of any of the non-sulfate surfactants. The preferred salts are the sodium or potassium salts, especially the sodium salts. The preferred taurate salt is the sodium sulfonate salt and the preferred sarcosinate salt is the sodium carboxylate salt. A preferred non-sulfate anionic surfactant is a combination of the N-alkyl, N-fatty acyl taurate sodium salt and the N-alkyl, N-fatty acyl sarcosinate sodium salt.

The complexation compound is a cationic compound, an amphoteric compound, a zwitterionic compound or a polyol compound. The amphoteric, cationic or zwitterionic nature of the compound is the result of combinations of a quaternary ammonium group, a carboxylate group, a sulfonate group, a polyol group, an amide group and an amine group.

The complexation amphoteric compound also may have a lipophilic component which may be an alkyl group, a polyether group, a polysulfide group or a polyamine group.

According to a second aspect of the invention, embodiments of the shampoo composition include optional components such as co-surfactants for enhancing foaming, lathering, and rich feel as well as ameliorating skin and eye irritation from other components. Co-surfactants especially preferred for such properties are betaines, sultaines, fatty acid polyols and amphoteric/zwitterionic surfactants. Additional embodiments of the shampoo composition include another optional component which is an anti-dandruff agent. Examples of the anti-dandruff agent include ketoconazole, climbazole, zinc pyrithione selenium disulfide, coal tar or sulfur. Selection of the optional components is made based on their compatibility with the non-sulfate surfactant and the amphoteric compound.

According to a third aspect, the present invention relates to a method of shampooing and conditioning hair through use of compositional embodiments of the invention. Embodiments of the method involve application of the shampoo composition to hair followed with or simultaneous with dilution with water. The neat shampoo (without water dilution) contains the coacervate of surfactant and complexation compound but in this arrangement, the concentration of surfactant or co-surfactant is sufficient to solubilize the coacervate. The dilution of the neat shampoo by water during the shampooing procedure causes at least some amount of the coacervate to precipitate. The coacervate precipitate deposits on the strands of hair and delivers smoothly conditioned hair.

According to a fourth aspect, the present invention relates to a kit comprising: (a) the shampoo composition of the invention and b) application instructions comprising the method according to the third aspect.

DETAILED DESCRIPTION OF THE INVENTION

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The term "about" is understood to mean±10 percent of the recited number, numbers or range of numbers.

The term "about 0 wt percent" is understood to mean that no substance, compound or material to which zero (0) refers is present, up to a negligible but detectable amount is present, assuming that the detectability can be determined on a parts per million basis.

The term "hydrogen bonding" is understood to mean a compound or group that contain a hydroxyl group or a hydrogen that is part of a polar group, such as but not limited to an amine, a carboxylic acid, a urethane group, a urea group and other similar groups and that can form molecule to molecule interaction through electrostatic or ionic interaction between positive and negative dipolar or ionic groups.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1 percent to about 5 percent" or "about 0.1 percent to 5 percent" should be interpreted to include not just about 0.1 percent to about 5 percent, but also the individual values (e.g., 1 percent, 2 percent, 3 percent, and 4 percent) and the sub-ranges (e.g., 0.1 percent to 0.5 percent, 1.1 percent to 2.2 percent, 3.3 percent to 4.4 percent) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Synthetic keratin fibers include polyamides, polyacrylic and polyester fibers, especially polyamic fibers which are used for artificial hair implantation. A preferred kind of hair as used herein, means mammalian hair including scalp hair, facial hair and body hair, particularly on hair on the human head and scalp.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. "QS" means sufficient quantity for 100 percent.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50 percent relative humidity. All such weights as they pertain to listed ingredients are based on the active level and do not include carriers or by-products that may be included in commercially available materials, unless otherwise specified.

The term "substantially free from" or "substantially free of" as used herein means less than about 1 percent, or less than about 0.8 percent, or less than about 0.5 percent, or less than about 0.3 by total weight of the composition.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerization of two or more monomers. The term "polymer" as used herein shall include all materials made by the polymerization of monomers as well as natural polymers. A polymer is formed of repeated covalent bonding of monomeric units such that the weight average molecular weight of the polymer is at least about 750 Da to 1250 Da. An oligomer is formed of repeated covalent bonding of monomeric units such that the weight average molecular weight of the oligomer ranges from that of at least two units to the lower limit wmw of a polymer. An oligomer is typically is based upon a small number of repeating monomeric units that can be incorporated by covalent bonding or by non-covalent bonding into a larger polymeric material. A polymeric resin includes oligomers and polymers and can contain reactive components for cross-linking, chain extension, side chain formation and chemical group formation such as ester, amide, ether, olefinic coupling and similar functional group formulation. Polymers made from only one type of monomer are called homopolymers. Polymers made from two or more different types of monomers are called copolymers. The distribution of the different monomers can be calculated statistically or block-wise-both possibilities are suitable for the present invention. Except if stated otherwise, the term "polymer" used herein includes any type of polymer including homopolymers and copolymers.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as daltons (Da), kilo Daltons (kDa) and mega Daltons, which is million daltons or (MDa). The acronym wmw stands for weight average molecular weight. Polydispersity is a unit-less number and indicates the breadth of the Gaussian curve plotted as the molecular weight of individual molecules (X axis) against the number of molecules at each molecular weight (Y-axis).

"Kit," as used herein, means a packaging unit comprising a plurality of components. An example of a kit is, for example, a first composition and a separately packaged second composition. Another kit may comprise a first composition and an energy delivery device. A different kit may comprise three different types of separately packaged composition and a hair styling implement. A further kit may comprise application instructions comprising a method and a composition/formulation.

The term "coacervate" as used herein, means the complex which forms between non-sulfate surfactant and complexation compound that may either be soluble or insoluble in the neat composition, typically forming a soluble complex in the neat composition, and which becomes less soluble upon dilution thus yielding an increase in its level of phase separation or precipitation from solution. Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletrics, Vol. 106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid and Interface Science, Vol. 140, No. 1, November 1990, pp 227-238.

The term "floc" as used herein, means localized clusters of agglomerated, insoluble coacervate, which may comprise polymer, surfactant, water and dispersed phases present in the composition such as anti-dandruff active and silicon emulsion. Any floc size disclosed herein is obtained using the Lasentec FBRM Method, which is described below.

The term "isotropic" as used herein, means a particular phase structure of coacervate wherein the structure is "identical along any three orthogonal directions in space, and is therefore dark or 'nonbirefringent' when viewed between crossed polarized light. (One direction is 'orthogonal' to another if the vector component of the first, in the direction of the second, is zero.) (Laughlin, R. G. (1994). "The Aqueous Phase Behavior of Surfactants," 182, 8.2).

The term "charge density" as used herein, means the ratio of the number of positive charges on a monomeric unit (of which a polymer is comprised) to the M.Wt. of said monomeric unit. The charge density multiplied by the polymer M.Wt. determines the number of positively charged sites on a given polymer chain.

The term "(meth)acryl" as used herein means methylacryl or acryl and can pertain to acid, amide or any derivative based on the (meth)acryl group. For example, the term "(meth)acrylic acid" as used herein means acrylic acid and/or methacrylic acid.

The terms "zwitterionic surfactant" and "amphoteric surfactant" as used herein mean respectively an organic compound (i.e., a zwitterionic surfactant) having a positively charged group (such as a quaternary ammonium group) and a negatively charged group (such as a carboxylate, sulfonate, sulfate, phosphate or phosphonate group) bound to an aliphatic divalent group and an organic compound (i.e., an amphoteric surfactant) having a Bronsted base group (such as a primary, secondary or tertiary amine) and a Bronsted acid group (such as carboxylic, sulfonic, sulfuric, phosphoric or phosphonic acid) bound to an aliphatic divalent group.

Examples of such surfactants include betaines, sultaines and similar positive and negative charge compounds.

The Composition

The embodiments of the composition according to the first aspect of the invention are mild cleansing agents that do not ameliorate the ability of the hair and skin to continue to provide oils and emollients to the hair. The embodiments of the composition also do not cause eye irritation as is common for shampoos containing detersive sulfate surfactants. The embodiments of the composition include one or more non-sulfate surfactants and one or more complexation compounds.

In use during the shampoo process, the solubilized coacervate of the non-sulfate surfactant and the complexation compound at least in part precipitates and at least partially coats the hair and remains following the shampoo and rinse steps. The coacervate precipitate delivers a silken, clean feel, no agglomeration or clumping and free flow to the hair. In short, the coacervate provides long lasting, desirable conditioning of the hair. These features according to the first aspect, as well as the other aspects and other relevant components, are described in detail hereinafter. All components of the composition described herein should be physically and chemically compatible with the essential components described herein, and should not otherwise unduly impair product stability, aesthetics or performance. The pH of the composition may be from about pH 3 to about pH 9, preferably from about pH 4 to about pH 7.

The embodiments of the composition comprise at least (a) a non-sulfate anionic surfactant and (b) a complexation compound. In considering the performance characteristics, such as coacervate formation, wet conditioning performance, dry conditioning performance, and conditioning agent deposition on hair, it is desirable to optimize the levels and combinations of non-sulfate anionic surfactant and complexation compound in order to maximize the performance potential of composition. In one embodiment, the non-sulfate anionic surfactant-complexation compound system for use in the composition comprises a non-sulfate anionic surfactant in combination with a complexation compound in which the amount of non-sulfate anionic surfactant relative to the amount of the complexation compound is in a weight to weight ratio range of about 90:1 to about 10:1, preferably about 75:1 to about 20:1, mom preferably about 65:1 to about 20:1, most preferably about 50:1 to about 25:1, especially most preferably about 40:1 to about 30:1 with preferred exemplary ratios being about 70:1, about 60:1, about 50:1 and about 40:1 with a concentration variability for each exemplary ratio of about 10% to about 15%. If an optional co-surfactant such as an amphoteric or nonionic surfactant is included with the non-sulfate anionic surfactant, the most preferred ratio of surfactant mixture to complexation compound is in a weight to weight ratio range of about 60:1 to 30:1, preferably about 50:1 to about 20:1, more preferably about 40:1 to about or about 20:1 and an exemplary ratio is about 25:1 along with the concentration variability for exemplary ratios the same as given above. Moreover, the most preferred weight to weight ratio range of non-sulfate anionic surfactant to complexation compound is as given above for exemplary ratios. For broader ratio ranges of non-sulfate anionic surfactant to complexation compound, the addition of optional amphoteric surfactant adds a minor amount to the surfactant number. For example, the ratio range of 90:1 to 10:1 would become 90+:1 to 10+:1 where the (+) sign indicates a slightly larger value.

Percentages of the complexation compound relative to the weight of surfactant plus complexation compound follow these ratios so that the ratios translate roughly to a percentage range of about 1 wt % to about 34 wt %, preferably about 1 wt/a to about 20 wt %, more preferably about 1 wt % to about 10 wt %, most preferably about 2 wt % to about 5 wt %. While all of the surfactant and all of the complexation compound do not form coacervate in the neat shampoo or coacervate precipitate during the shampooing process, these ratios assure that reasonable amounts of coacervate are formed for conditioning the hair. According to the invention, the combination of such a non-sulfate anionic surfactant with the complexation compound with these ratios provides enhanced deposition of the coacervate conditioning complex to hair and/or skin without reducing cleansing or lathering performance.

In embodiments of the invention, the non-sulfate surfactant comprises from about 5 percent to about 70 percent, or from about 8 percent to about 50 percent, or from about 10 percent to about 40 percent by weight, more preferably about 5 percent to about 50 percent, most preferably about 10 percent to about 25 percent relative to the total weight of the composition. More particularly, the embodiments of the composition of the invention include an amount of the N-fatty acyl taurate salt ranging from about 0.1 wt percent to about 35 wt percent and an amount of the N-fatty acyl sarcosinate salt ranging from about 0.1 wt percent to about 35 wt percent, with both wt percentages being relative to the total weight of the composition. Preferably, the amounts of the N-fatty acyl taurate salt and N-fatty acyl sarcosinate salt each range from about 0.1 wt percent to about 20 wt percent, more preferably from about 0.5 wt percent to about 8 to 10 wt percent. A specific embodiment of the composition includes about 4 wt percent to 6 to 8 wt percent of each of the N-olcyl, N-methyl taurate sodium salt and the N-lauroyl sarcosinate sodium salt.

The concentrations of surfactant and complexation compound are also factors in formation of reasonable amounts of coacervate. Given the total concentration of surfactant present in the composition, the foregoing ratios provide guidance for the concentration of complexation compound to be included.

Preferred exemplary embodiments of the composition of the invention which contain the N-fatty acyl taurate salt and N-fatty acyl sarcosinate salt (i.e., the combination of sulfate free surfactants) include an amount of the especially preferred complexation compound, polyquarternium-10, ranging from about 0.05 wt percent to about 20 wt percent, preferably about 0.1 wt percent to about 10 wt percent, more preferably about 0.1 wt percent to about 5 wt percent, most preferably about 0.1 wt percent to about 2 wt percent relative to the total weight of the composition and exemplary weight percentages of polyquarternium-10 are about 0.1 wt percent with a concentration variation for this exemplary weight percentage of about 10% to about 15% by weight.

Description of the Surfactant

The non-sulfate surfactant is an amino acid derivative and includes an N-fatty acyl taurate salt or an N-fatty acyl sarcosinate salt, the N-alkyl derivatives thereof or any combination thereof. The taurate and sarcosinate surfactants have the following formulas wherein R represents the fatty group of the fatty acyl substituent, R' is hydrogen or alkyl and M represents the metal ion including sodium and potassium, especially sodium.

| RCONR'CH2CH2SO3M | RCONR'CH2CO2M |
|---|---|
| N-fatty acyl taurate salt | N-fatty acyl sarcosinate salt |

The N-fatty acyl group for the taurate salt may be any longer chain saturated or unsaturated fatty group. Preferably, the fatty acyl group for the taurate salt is an unsaturated fatty acyl group of 12 to 22 carbons, preferably 14 to 20 carbons, more preferably 14 to 18 carbons including myristoyl, palmitolyl, sapienoyl, oleyl, elaidoyl and vaccinoyl acyl groups, most preferably oleyl and palmitoyl acyl groups, especially most preferably the oleyl group. The N-alkyl group is a C1 to C6 linear or branched alkyl group, preferably methyl, ethyl, propyl or isopropyl and more preferably methyl.

The N-fatty acyl group for the sarcosinate salt may be any shorter chain saturated fatty group. Preferably the fatty acyl group for the sarconinate salt is a saturated fatty acyl group of 6 to 14 carbons including caproloyl, enanthoyl, capryloyl, pelargonoyl, caproyl, undecyloyl, lauroyl, tridecyloyl and myristoyl groups, more preferably 8 to 12 carbons, and most preferably the lauroyl C12 acyl group. The N-alkyl group is the same as that for the taurate salt except that R' as hydrogen is excluded. R' for the sarconsinate salt is preferably methyl.

An especially preferred non-sulfate surfactant is a combination of N-oleyl N-methyl taurate sodium salt and N-lauroyl sarcosinate sodium salt.

Description of the Complexation Compound

The embodiments of the composition of the invention also include the complexation compound. The complexation compound may be a cationic compound or polymer, such as a quaternary ammonium organic compound, a betaine compound, a sultaine compound, a diamino carboxylic acid compound or a fatty acid polyol estr compound. These complexation compounds are derivatives of amine/quaternary ammonium compounds, amino acids, hydroxyl amino acids or fatty acid polyol esters. They can function as conditioners as well as mild to medium strength surfactants. They have reduced irritation properties and do not cause irritation to sensitive skin. Preferred complexation compounds are the cationic compounds having only a positive charged group, such as but not limited to quaternary ammonium compounds.

More specific embodiments of the complexation compound include a quaternary ammonium compound or polymer, a fatty acyl aminoalkyl betaine, a fatty acyl betaine, a fatty acyl aminopropyl sultaine, a fatty acyl sultaine, a N-fatty acyl aminoalkyl glycine, a glyceryl fatty acid ester, an N-fatty acyl, an N-aminoalkyl, N-hydroxyalkylamino acid wherein the amino acid is glycine, alanine, valine, leucine, isoleucine or phenyl alanine, and any combination of any of these more specific embodiments. Examples include quaternary ammonium hydroxyethyl cellulosic, (N-trimethylaminoethyl or propyl (meth)acrylamide)/methacrylamide copolymer, (trimethylaminoethyl (meth)acrylate)/ethyl or methyl (meth)acrylate copolymer, cocobetaine, cocamidopropyl betaine, a mixture of caprylamidopropyl betaine and capramidopropyl betaine, cocahydroxysultaine, cocamidopropylhydroxysultaine, sodium cocoamphoacetate, disodium cocoamphodiacetate, sodium cocoamphopropionate, disodium cocoamphodipropionate, glyceryl laurate, glyceryl myristate and any combination thereof.

Further embodiments of the complexation compound include cationic derivatives of natural polysaccharides such as cellulose, glucomannan, starch, xanthan gum, gellan, pullulan, dextran, arabic gum, carrageenan, gum tragacanth, locust bean gum and similar natural gums, complex polysaccharides and polysaccharide derivatives. For example, cellulose, starch and dextrans can be converted to partially soluble derivatives through chemical manipulation of glucose unit hydroxyl groups such as by formation of hydroxyethyl, hydroxypropyl, carboxyl and similar pendant groups. The cationic derivatives can be formed by addition of pendant aminoalkyl groups and quaternizing the amine group with methyl iodide. Examples include quaternium-10, quaternized glucomannan, and quaternized hydroxypropyl carboxymethyl cellulose.

In additional embodiments, the complexation compound may be a cationic copolymer such as a polymerization product of a (meth)acrylamide or alkyl (meth)acrylate monomer and a cationic monomer, wherein the cationic monomer is selected from the group consisting of: dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl(meth) acrylate methyl sulphate, dimethylammonium ethyl(meth) acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride, and mixtures thereof. The cationic derivatives can be formed by quaternizing the amine groups with methyl iodide.

In further embodiments of the complexation compound, the foregoing polymerization produce may include a cationic monomer selected from the group consisting of: cationic monomers include trimethylammonium ethyl(meth) acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, and mixtures thereof.

In yet other embodiments of the complexation compound, the cationic copolymer can be water-soluble. It may be formed from (1) copolymers of (meth)acrylamide and cationic monomers based on (meth)acrylamide, and/or hydrolysis-stable cationic monomers, (2) terpolymers of (meth) acrylamide, monomers based on cationic (meth)acrylic acid esters, and monomers based on (meth)acrylamide, and/or hydrolysis-stable cationic monomers. Monomers based on cationic(meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl(meth)acrylates with C1 to C3 in the alkyl and alkylene groups. In an embodiment, the cationized esters of the (meth)acrylic acid containing a quaternized nitrogen atom are selected from the group consisting of: ammonium salts of dimethylaminomethyl(meth)acrylate, dimethylaminoethyl(meth)acrylate, dimethylaminopropyl(meth)acrylate, diethylaminomethyl(meth)acrylate, diethylaminoethyl (meth)acrylate; and diethylaminopropyl(meth)acrylate quaternized with methyl chloride. In an embodiment, the cationic esters of the (meth)acrylic acid containing a quaternized nitrogen atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl (meth) acrylamide, all monomers that can be regarded as stable to hydrolysis. In an embodiment, the cationic monomer is hydrolytically stable and the hydrolytically sis-stable cationic monomer is selected from the group consisting of: diallyl dimethylammonium chloride and water-soluble, cationic styrene derivatives.

In yet another embodiment, a useful class of quaternary ammonium compounds serving as the complexation compound is the class of quaternized phosphate esters, as depicted in general structural formula:

$$\left[ (YO)_{p\text{-}3} \overset{O}{\underset{\parallel}{P}} \left( A - \overset{R_8}{\underset{\underset{R_9}{\mid}}{\overset{\mid}{N^{\oplus}}}} - (CH_2)_m - \overset{R_7}{\underset{\mid}{N}} - \overset{O}{\underset{\parallel}{C}} - R_6 \right)_p \right]^{+P} pZ^-$$

Wherein R6 is an aryl, an alkaryl, a saturated or unsaturated alkyl group, or a saturated or unsaturated hydroxyalkyl group, wherein the alkyl or hydroxyalkyl group includes about seven to about 21 carbon atoms; R7 is hydrogen, or an alkyl or a hydroxyalkyl group including one to about six carbon atoms; R8 and R9, independently, are an alkyl or a hydroxyalkyl group including one to about six carbon atoms; A is a residue of a glycol or a triol having two to about four carbon atoms, such as the residue of propylene glycol (—OCH2CH(OH)CH2-); Z is an anion selected from the group consisting of chloride, bromide, methosulfate, ethosulfate, and combinations thereof; m is a numeral from one to about 10; Y is selected from the group consisting of hydrogen, an alkyl group, a hydroxyalkyl group, and an aryl group, either substituted or unsubstituted, and wherein the alkyl or the hydroxyalkyl group includes one to about 22 carbon atoms; and p is a number from 1 to 3. To achieve the full advantage of the present invention, the quaternized phosphate ester is a quaternized phosphate diester that includes the alkyl moiety of an essential fatty acid, like linoleic acid, arachidonic acid or ricinoleic acid, as the R6 substituent of the compound. For example, the quaternized phosphate ester of general structural formula below that includes the alkyl moiety of an essential fatty acid as the R6 substituent and wherein the number is 2.

foregoing desired attributes while not engaged as the complexation compound. These co-surfactants may be selected from the group consisting of: amphoteric surfactants, zwitterionic surfactants, cationic surfactants, non-ionic surfactants, and mixtures thereof. The concentration of such co-surfactants may be from about 0.5 percent to about 20 percent, or from about 1 percent to about 10 percent, by total weight of the composition. In an embodiment, the composition comprises a co-surfactant selected from the group consisting of: amphoteric surfactants, zwitterionic surfactants, and mixtures thereof. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In an embodiment, the amphoteric surfactant is selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium comamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine comamphopropionate, triethanonlamine lauraminopropionate, triethanonlamine lauroamphoacetate, trietha- $$\left[ \left( CH_3-(CH_2)_3-CH=CH-CH_2-CH=CH-CH_2-\overset{O}{\underset{\parallel}{C}}-NH-(CH_2)_3-\overset{CH_3}{\underset{CH_3}{\overset{\mid}{\underset{\mid}{N^{\oplus}}}}}-CH_2-\overset{OH}{\underset{\mid}{CH}}-CH_2-O \right)_2 \overset{O}{\underset{\parallel}{P}}-O^-Na^+ \right]^{*2} 2\,Cl^-$$

Optional Components of the Composition

Cosurfactants

The composition with the non-sulfate surfactant system may comprise an additional co-surfactant that functions primarily to contribute foaming, lathering, amelioration of skin and eye irritation, emollient and softening properties to human tissues, skin, hair and the like. While these co-surfactants are similar to and/or overlap to some extent with the complexation compounds which form coacervates with the non-sulfate surfactants, these co-surfactants are included in embodiments of the composition in addition to the complexation compounds. An additional amount and/or a different co-surfactant can be employed to contribute to the nonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydoxypropylsulfonate, disodium cocoamphodiacetate, disodium cocoamphodipropionate, disodium dicarboxyethylcocopopylenediamine, disodium laureth-5 carboxyamphodiacetate, disodium lauriminodipropionate, disodium lauroamphodiacetate, disodium lauroamphodipropionate, disodium olcoamphodipropionate, disodium PPG-2-isodecethy-7 carboxyamphodiacetate, lauraminopropionic acid, lauroamphodipropionic acid, lauryl aminopropylglycine, lauryl diethylcnediaminoglycine, and mixtures thereof.

In an embodiment, the amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

In a further embodiment, the co-surfactant may be a zwitterionic surfactant, wherein the zwitterionic surfactant is a derivative of an aliphatic quaternary ammonium, phosphonium, and sulfonium compound also having an anionic group such as carboxy, sulfonate, sulfate, phosphate or phosphonate. The aliphatic radicals of the zwitterionic surfactant are straight or branched chain, and wherein one of the aliphatic substituents contains from about 8 to about 18 carbon atoms and one contains In an embodiment, the zwitterionic surfactant is selected from the group consisting of: cocamidoethyl betaine, cocamidopropylamine oxide, cocamidopropyl betaine, cocamidopropyl dimethylamino-hydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. In an embodiment, the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Examples of nonionic co-surfactants include Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, Polysorbate-65, Steareth-10, Sucrose Stearate, Laureth-4, PEG-8 Stearate, Sorbitan Laurate, Polyglyceryl-3 Methylglucose Distearate and mixtures thereof. In an embodiment, the co-surfactant is a zwitterionic surfactant, wherein the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Anti-Dandruff Active

The composition comprises an optional anti-dandruff active, which may be an anti-dandruff active particulate. In an embodiment, the anti-dandruff active is selected from the group consisting of: pyridinethione salts; zinc carbonate; azoles, such as ketoconazole, climbazole, econazole, and elubiol; selenium sulphide; particulate sulfur, keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form.

In an embodiment, the concentration of pyridinethione anti-dandruff particulate ranges from about 0.01 percent to about 5 percent, by weight of the composition, or from about 0.1 percent to about 3 percent, or from about 0.1 percent to about 2 percent. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable.

Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiabendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (iPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01 percent to about 5 percent, or from about 0.1 percent to about 3 percent, or from about 0.3 percent to about 2 percent, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbazole, salicylic acid and octopirox, and mixtures thereof.

The on-scalp deposition of the anti-dandruff active is at least about 1 microgram/cm2. The on-scalp deposition of the anti-dandruff active is important in view of ensuring that the anti-dandruff active reaches the scalp where it is able to perform its function. In an embodiment, the deposition of the anti-dandruff active on the scalp is from about 1.5 microgram/cm2 to about 10 microgram/cm2. The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Suspending Agent

The shampoo compositions of the present invention may further comprise a suspending agent at concentrations effective for suspending dispersed particles of a water insoluble, additional conditioning agent, or other water-insoluble, dispersed material in the shampoo compositions. Such concentrations range from about 0.1% to about 10%, preferably from about 0.3% to about 5.0%, by weight of the shampoo compositions. Suitable suspending agents include crystalline suspending agents that can be categorized as acyl derivatives, long chain amine oxides, or combinations thereof. These suspending agents are described in U.S. Pat. No. 4,741,855.

These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e. g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarboxyls having CS-C22 chains may be used.

Other long chain acyl derivatives suitable for use as suspending agents include N,N-dihydrocarbyl amido benzoic acid and soluble salts thereof (e.g., Na, K), particularly N,N di(hydrogenated) C16, C18 and tallow amidobenzoic acid species of this family.

Examples of suitable long chain amine oxides for use as suspending agents include alkyl (Cm-C22) dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

Dispersed Particles

The composition of the present invention may include dispersed particles such as but not limited to micron sized or micronized mica and/or silica. These particles may be added to modify opacity, pearl-essence, brilliance, volume, body and tactile sensing of the shampoo characteristics. In the compositions of the present invention, it is preferable to incorporate at least 0.025% by weight of the dispersed particles, more preferably at least 0.05%, still more preferably at least 0.1%, even more preferably at least 0.25%, and yet more preferably at least 0.5% by weight of the dispersed particles. In the compositions of the present invention, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles.

Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, Water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names.

The compositions of the present invention may also contain antimicrobial agents which are useful as cosmetic biocides such as benzoic acid and phenoxyethanol.

The compositions of the present invention may also contain chelating agents for complexing soil and impurities to be removed by washing the hair. The chelates include di, tri or tetraamine compounds and salts thereof.

Carrier for Composition

The composition comprises a cosmetically acceptable carrier. In an embodiment, the carrier is an aqueous carrier. The amount and chemistry of the carrier is selected according to the compatibility with other components and desired characteristic of the product. In an embodiment, the carrier is selected from the group consisting of: water and water solutions of lower alkyl alcohols. In an embodiment, the carrier is a lower alkyl alcohol, wherein the monohydric alcohol has 1 to 6 carbons. In an embodiment, the carrier is ethanol and/or isopropanol. In an embodiment, the cosmetically acceptable carrier is a cosmetically acceptable aqueous carrier and is present at a level of from about 20 percent to about 95 percent, or from about 60 percent to about 85 percent by weight relative to the total weight of the composition.

The features of the composition according to the first aspect, as well as the other aspects and other relevant components, are described in detail hereinafter. All components of the composition described herein should be physically and chemically compatible with the essential components described herein, and should not otherwise unduly impair product stability, aesthetics or performance.

In accordance with embodiments of the present invention, the personal care composition may further comprise one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. In an embodiment, the benefit agent is selected from the group consisting of: particles; colorants; perfume microcapsules; gel networks: other insoluble skin or hair conditioning agents such as skin silicones, natural oils such as sun flower oil or castor oil; and mixtures thereof.

Method of Application

According to the third aspect of the invention, the composition is applied as a shampoo to human hair while bathing, washing the hair, treating the hair in a salon or otherwise performing an operation involving cleaning the hair. In use, the shampoo composition cleans the hair of dirt, grease, particulate matter and other untoward, undesirable substances and/or materials on the hair. In use, the shampoo composition is applied as a normal shampoo. The hair may be dry or first wetted. An aliquot of the shampoo composition is applied and the hair agitated while rinsing with additional water.

The composition forms coacervate particles upon dilution of the composition with water. In use as a shampoo, the composition is applied to wet hair, the hair agitated with additional water whereby the coacervate precipitate or particles are formed. The coacervate precipitate deposits at least in part on the surfaces of the hair strands and is not dislodged by additional agitation, water rinsing and bathing. The coacervate precipitate provides conditioning to the hair such that the hair is lustrous, bouncy, not matted, not greasy and enable easy combing.

The percentage of coacervate particles with a floc size of greater than about 2 microns is minor to minimal owing to the clear to slightly cloudy appearance of at least some specific embodiments of the diluted shampoo according to the invention. While inclusion of pearlescent components, suspending agents, brilliance agents and inorganic particulates according to options of the invention will change the shampoo character from clear to opaque in neat and diluted forms, the coacervate particle size formed when the neat shampoo is diluted typically remains the same. At coacervate particle sizes greater than 2 microns the otherwise clear, diluted shampoo will exhibit light scattering and will appear turbid to opaque. In some instances, depending upon the weight to weight ratio of sulfate free anionic surfactant to complexation compound and upon the other optional components of the shampoo formulation, the diluted shampoo can exhibit turbidity and opacity from slight to moderate. The floc size can be measured after diluting the composition with water.

An example for measuring floc size may be based upon the Lasentec FBRM Method: In a suitable mixing vessel create a 1:9 to 1:50 dilution of composition in distilled water at ambient temperature and mix for 5 min at 250 rpm. Using a peristaltic pump transfer ambient distilled water into the mixing vessel at a rate of 100 g/min resulting in a final dilution of 1:50 parts composition to distilled water. After a 10 min equilibration period a Lasentec Focused Beam Reflectance Method (FBRM) [model S400A available from Mettler Toledo Corp] may be used to determine floc size and amount as measured by chord length and particle counts/sec (counts per sec).

The viscosity of the coacervate particles may be measured via squeeze flow resulting in a squeeze flow viscosity. The coacervate may be prepared and isolated for rheological testing as follows: A well-mixed 1:50 dilution of composition in distilled water is prepared at ambient temperature in such a quantity to produce a coacervate pellet of at least 3 grams after centrifugation at 4500 rpm for 30 min. The supernatant liquid is decanted and discarded and the coacervate pellet collected. A second centrifugation step is required for 15 min at 9100 rpm to ensure sample integrity prior to measurement. Any remaining supernatant liquid is removed without disturbing the coacervate pellet collected at the bottom of the container.

In the squeeze flow experiment, the coacervate can be tested according to the procedures outlined in U.S. Pat. No. 9,272,164, the disclosure of which is incorporated herein by reference.

According to the first and second aspects, the present invention relates to a hair shampoo and conditioning composition comprising: an aqueous mixture of (a) a non-sulfate surfactant combination of sodium methyl oleyl taurate and sodium lauroyl sarcosinate at a weight percent each of from about 4 wt % to about 6 wt % and (b) a complexation compound of a quaternary ammonium cellulosic derivative at a weight percent of about 0.4 wt %, c) a co-surfactant of cocamidopropyl betaine at a weight percent of about 0.1 wt %, and d) zinc pyrithione particles at a weight percent of about 0.01 wt %, all weight percentages being relative to the total weight of the composition.

The third aspect relates to the use of the composition, according to the first aspect, for treating hair. In an embodiment, the use is for achieving improved hair feel and/or for reducing dandruff. The details of the composition described in relation to the first aspect also apply to the composition of the second aspect.

The fourth aspect relates to a kit comprising: (a) application instructions comprising the method according to the second aspect; and (b) a composition according to the first aspect. In an embodiment, the composition of the kit is the composition according to the first aspect. The details of the composition described in relation to the first aspect also apply to the kit.

EXAMPLES

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified.

It has been surprisingly discovered that the shampoos composition of sulfate free surfactant and complexation compound such as a cationic surfactant delivers an unexpected high hair conditioning effect. In particular, the composition of Sodium Methyl Oleoyl Taurate and Sodium Lauroyl Sarcosinate with polyquarternium-10 and especially with low levels of polyquarternium-10 delivers an unexpected high hair conditioning effect.

Half head tests done by stylists show these hair conditioning performance advantages of the sulfate free SH according to the present invention in comparison to a reference/market shampoo with sulfate based surfactants (. Half-head comparisons enable the hairstylist to evaluate the effects of hair products in comparison with a defined standard. This involves a sample of the test product being applied to the head of one model, and then being directly compared to a comparison sample or the untreated hair according to various technical hairstyling criteria. This test is termed a half-head comparison because the test samples are applied to one half the head respectively, thus enabling a direct comparison under absolutely identical test conditions (identical hair structure, degree of damage, hair colour etc.). The performance of the sulfate free shampoo according to the present invention (example 1) was compared with the performance of the reference/market shampoo. The following hair care criteria were judged by experienced stylists: Rinseability, Wet Combability, Dry Combability, Dry Feel, Hair Shine.

Half head test are carried out with 3 test persons, the numbers indicated for how many test persons each criterion was judged how:

| Criterion | Example 1 better than reference shampoo | Example 1 equal than reference shampoo | Example 1 worse than reference shampoo |
|---|---|---|---|
| Rinseability | — | 3 | — |
| Wet Combability* | 3 | — | — |
| Dry Feel* | 3 | — | — |
| Hair Shine | — | 2 | 1 |

*signifcant difference (p > 0.85)

Reference shampoo: Sodium Lauryl Ethersulfate/Cocamidopropyl Betaine based, cationic polymer composition: 0.3 wt/o Polyquarternium-10, 0.12 wt % Polyquarternium-6, 0.178% Guar Hydroxypropyltrimonium Chloride, 0.5% Amodimethicone The results indicated clearly that the shampoo according to the present invention leads to better wet combability and dry feel, the 2 key criteria to evaluate the conditioning performance of a shampoo, despite the fact that the reference shampoos contains 0.598 wt % cationic polymers and 0.5% Amodimethicone, a known silicone based hair conditioning agent, so more than 1% active conditioning agents, whereas the shampoo according to the present invention contains 0.4% cationic polymer only, 36% of the conditioning actives level of the sulfate surfactant based reference shampoo. Net—the shampoo according to the present invention has an unexpected and much higher effectiveness on coacervate formation than average sulfate surfactants based shampoos.

Examples

1.

| Raw Material | Amount |
|---|---|
| Sodium Methyl Oleoyl Taurate | 2.5 g |
| Sodium Lauroyl Sarcosinate | 1.5 g |
| Cocamidopropyl Betaine | 4.5 g |
| Polyquaternium-10 | 0.4 g |
| Citric Acid | 0.4 g |
| Sodium Benzoate | 0.4 g |
| Perfume | 0.5 g |
| Water | to 100 g |

-continued

2.

| Raw Material | Amount |
|---|---|
| Sodium Methyl Oleoyl Taurate | 2.5 g |
| Sodium Lauroyl Sarcosinate | 3.0 g |
| Sodium Cocoamphodiacetate | 3.8 g |
| Polyquaternium-10 | 0.2 g |
| Citric Acid | 0.4 g |
| Sodium Benzoate | 0.4 g |
| Perfume | 0.5 g |
| Water | to 100 g |

3.

| Raw Material | Amount |
|---|---|
| Sodium Methyl Oleoyl Taurate | 2.5 g |
| Sodium Lauroyl Sarcosinate | 3.0 g |
| Cocamidopropyl Betaine | 4.5 g |
| Guar Hydroxypropyltrimonium Chloride | 0.2 g |
| Citric Acid | 0.5 g |
| Sodium Benzoate | 0.4 g |
| Perfume | 0.5 g |
| Water | to 100 g |

4.

| Raw Material | Amount |
|---|---|
| Sodium Methyl Oleoyl Taurate | 2.8 g |
| Sodium Lauroyl Sarcosinate | 2.5 g |
| Coco Betaine | 4.0 g |
| Polyquaternium-6 | 0.15 g |
| Citric Acid | 0.3 g |
| Sodium Benzoate | 0.4 g |
| Perfume | 0.5 g |
| Water | to 100 g |

5.

| Raw Material | Amount |
|---|---|
| Sodium Methyl Oleoyl Taurate | 2.5 g |
| Sodium Lauroyl Sarcosinate | 2.0 g |
| Cocamidopropyl Hydroxysultaine | 4.0 g |
| Linolamidopropyl PG-Dimonium Chloride Phosphate | 0.4 g |
| Citric Acid | 0.3 g |
| Sodium Benzoate | 0.4 g |
| Perfume | 0.5 g |
| Water | to 100 g |

Test Methods

Half Head Tests

Half-head comparisons enable the hairstylist to evaluate the effects of hair products in comparison with a defined standard. This involves a sample of the test product being applied to the head of one model, and then being directly compared to a comparison sample or the untreated hair according to various technical hairstyling criteria. This test is termed a half-head comparison because the test samples are applied to one half the head respectively, thus enabling a direct comparison under absolutely identical test conditions (identical hair structure, degree of damage, hair colour etc.).

The selection of models is as random as possible, although the following guidelines must be met:

A hair diagnosis establishes whether the model is suitable for the planned half-head comparison Hair structure must be commensurate with the type of product to be tested, e.g. normal hair structure for normal hair conditioning products, coloured hair for coloured hair conditioning products etc.

Hair should be at least 12 cm long so that feel and combability can be assessed correctly The amount of hair of each model should be big enough to enable a clear-cut assessment Hairstyles should be symmetrical; otherwise the hair may be thicker on one half than the other Each model's hair is washed twice with neutral shampoo and subsequently towel-dried. The towel-dried hair is then parted in the middle into two sections from brow to neck. One of the sections is treated with the present invention (example 1), the example 1 of patent JP 3,616,154 being applied to the other section, whereby the same quantity of product must be applied to both sections (amount depending on hair length).

Evaluation Criteria Half Head Tests:

Rinseability:

Evaluation here is of whether a shampoo is easier or more difficult to wash out of the hair after shampooing.

Wet and Dry Combability:

Combability of the hair is assessed by placing an aluminium comb parallel to the middle parting and running it through the hair to the shoulder. The comb must remain at a 90° angle throughout and also remain in contact with the scalp throughout combing in order to avoid varying comb angles. The amount of resistance/effort needed during combing is the basis for evaluating the product as easier to comb/more difficult to comb. This test can be carried out on wet hair and on dry hair as well.

Dry Feel:

When the hair is completely dry, the evaluating stylist assesses the dry feel of the hair. This is assessed by running the hair from root to end between the thumb and middle and index fingers, while simultaneously applying light pressure; or alternatively, by running lightly outspread fingers through the hair from root to end. If the hair runs easily through the fingers, this is referred to as a smooth feel; if the hair is impeded from running easily through the fingers, this is referred to as a coarse feel.

Hair Shine:

Hair shine is evaluated by looking at the reflection of light on the hair under standard conditions (natural daylight or a daylight lamp). From a distance of 0.5 m, and with slight head movements by the model, the light reflection or shine is evaluated as more/less.

Summary Statements

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A composition for hair cleansing and conditioning, consisting of:

an aqueous mixture of a non-sulfate anionic surfactant, a complexation compound, a co-surfactant, an optional anti-dandruff agent and an optional component, wherein:

the composition is free of any kind of silicone and sulfate anionic surfactant;

the non-sulfate anionic surfactant is a combination of an N-fatty acyl taurate salt and an N-fatty acyl sarcosinate salt, the N-alkyl derivatives thereof or any combination thereof;

the complexation compound is a quaternary ammonium hydroxyethyl cellulose, a quaternary ammonium hydroxypropyl cellulose, a quaternary ammonium carboxyl cellulose, a quaternary ammonium phosphate ester of the formula $(YO)_{3-m}$—P(O)—[O—$CH_2CHOHCH_2$—$N^+(CH_3)_2$—$CH_2$—$CH_2$—$CH_2$—NH—C(O)—$R^6]_m(Z^-)_m$ wherein $R^6$ is a saturated or unsaturated C7-C21 alkyl group, Y is a C1 to C22 alkyl, Z is chloride, bromide, methosulfate or ethosulfate, and m is 1, 2 or 3, and any combination thereof;

the co-surfactant is a betaine compound, or a sultaine compound, or a mixture thereof;

the optional anti-dandruff agent is climbazole, ketoconazole, zinc pyrithione, selenium disulfide, coal tar or sulfur;

the optional component is one or more of a suspending agent, a dispersed micronized mica, a dispersed micronized silica, vitamin B1 or derivative thereof, vitamin B2 or derivative thereof, vitamin B6 or derivative thereof, vitamin B12 or derivative thereof, vitamin C or derivative thereof, pantothenic acid or derivative thereof, pantothenyl ethyl ether or derivative thereof, pantenol or derivative thereof, biotin or derivative thereof, a water soluble amino acid or salt thereof, a water insoluble amino acid or salt thereof, a pigment material, a botanical color, a natural color, an antimicrobial agent, or a di, tri or tetramine chelating agent or salt thereof; and, at least a first portion of the non-sulfate anionic surfactant and the complexation compound form a coacervate and the coacervate is solubilized in the aqueous mixture by the co-surfactant or a combination thereof with the non-sulfate anionic surfactant.

2. The composition of claim 1 wherein the weight ratio range of the complexation compound relative to the combination of weights of the non-sulfate anionic surfactant, the co-surfactant and the complexation compound is from about 1 wt % to about 10 wt %.

3. The composition of claim 2 wherein the weight ratio range is from about 2 wt % to about 5 wt %.

4. The composition of claim 1 wherein the coacervate forms a precipitate upon dilution of the composition with water.

5. The composition of claim 1 wherein the fatty acyl group of the N-fatty acyl taurate salt is an acyl moiety of an unsaturated fatty acid of 12 to 22 carbons and the fatty acyl group of the N-fatty acyl sarcosinate salt is an acyl moiety of a saturated fatty acid of 5 to 10 carbons.

6. The composition of claim 1 wherein the fatty acyl group of the N-fatty acyl taurate salt is an oleoyl moiety and the fatty acyl group of the N-fatty acyl sarcosinate salt is a lauroyl moiety.

7. The composition of claim 1 wherein the complexation compound is the quaternary ammonium hydroxyethyl cellulose.

8. The composition of claim 1 including an antidandruff agent.

9. The composition of claim 1 wherein the complexation compound is-the quaternary ammonium phosphate ester.

10. A method for washing hair comprising applying the composition for hair cleansing and conditioning of claim 1 to the hair, diluting the composition on the hair with at least a ten fold excess of water thereby forming a coacervate precipitate and agitating the diluted composition on the hair thereby producing washed hair having deposited thereon the coacervate precipitate.

11. The method of claim 10 further comprising rinsing the washed hair with water.

12. The method of claim 11 wherein the coacervate precipitate remains on the hair after rinsing the washed hair.

13. The method of claim 12 which provides the coacervate as a softener and conditioner of the hair.

14. The method of claim 10 wherein the composition includes an antidandruff agent.

* * * * *